(12) United States Patent
MacArthur

(10) Patent No.: US 8,851,889 B2
(45) Date of Patent: Oct. 7, 2014

(54) PLACEMENT TOOL

(76) Inventor: Jonathan MacArthur, London (CA)

(*) Notice: Subject to any disclaimer, the term of this patent is extended or adjusted under 35 U.S.C. 154(b) by 0 days.

(21) Appl. No.: 13/262,689

(22) PCT Filed: Apr. 1, 2010

(86) PCT No.: PCT/CA2010/000515
§ 371 (c)(1),
(2), (4) Date: Dec. 14, 2011

(87) PCT Pub. No.: WO2010/111793
PCT Pub. Date: Oct. 7, 2010

(65) Prior Publication Data
US 2012/0082953 A1 Apr. 5, 2012

Related U.S. Application Data

(60) Provisional application No. 61/202,770, filed on Apr. 2, 2009.

(51) Int. Cl.
A61C 3/00 (2006.01)
A61C 5/06 (2006.01)
A61C 5/04 (2006.01)

(52) U.S. Cl.
CPC *A61C 5/062* (2013.01); *A61C 5/045* (2013.01)
USPC ............................................. 433/141

(58) Field of Classification Search
USPC .................................... 433/32, 141
See application file for complete search history.

(56) References Cited

U.S. PATENT DOCUMENTS

| | | | | | |
|---|---|---|---|---|---|
| 214,923 | A | * | 4/1879 | Justi | 433/141 |
| 1,687,179 | A | * | 10/1928 | Peterson | 206/15.3 |
| 2,170,681 | A | * | 8/1939 | Finlayson | 219/421 |
| 2,236,837 | A | * | 4/1941 | Rimmel | 219/421 |
| 4,262,820 | A | | 4/1981 | Flint | |
| 4,959,199 | A | * | 9/1990 | Brewer | 422/300 |
| 4,993,949 | A | * | 2/1991 | Hill | 433/141 |
| 5,256,064 | A | * | 10/1993 | Riihimaki et al. | 433/141 |
| 5,320,533 | A | | 6/1994 | Lee | |
| 5,525,059 | A | * | 6/1996 | Lee | 433/141 |
| 5,575,649 | A | * | 11/1996 | Lee | 433/141 |
| 5,669,771 | A | * | 9/1997 | Lee | 433/218 |
| 5,775,344 | A | * | 7/1998 | Clay | 132/218 |
| 7,108,438 | B2 | * | 9/2006 | Fontaine | 401/1 |

FOREIGN PATENT DOCUMENTS

FR 2912641 A1 8/2008

OTHER PUBLICATIONS

International Search Report issued by the Canadian Intellectual Property Office dated Jul. 14, 2010 for corresponding International Application No. PCT/CA2010/000515 filed Apr. 1, 2010.
Written Opinion of the International Searching Authority issued by the Canadian Intellectual Property Office dated Jul. 14, 2010 for corresponding International Application No. PCT/CA2010/000515 filed Apr. 1, 2010.

* cited by examiner

*Primary Examiner* — Ralph Lewis

(57) ABSTRACT

The present invention provides an improved pre-loaded placement tool (10) useful for positioning small objects. The head portion (14) of the placement tool (10) is pre-loaded with a heat-activated adhesive (16) and the body (12) of tool (10) includes a flange (18) cooperating with receiving bracket (24) of a heating device (20).

4 Claims, 4 Drawing Sheets

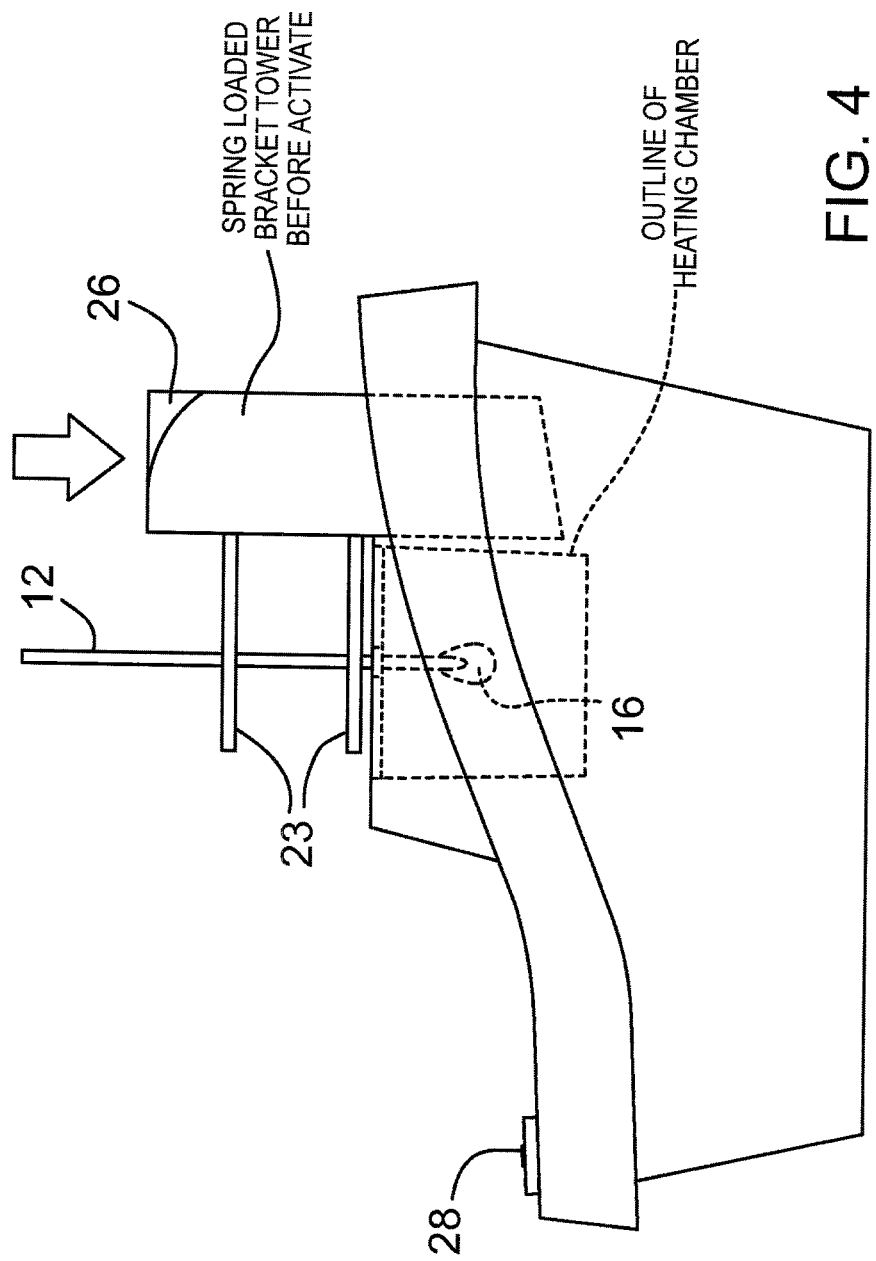

PLACEMENT TOOL

FIELD OF THE INVENTION

The present invention provides a simple and reliable method of retaining small objects so that they may be placed accurately and precisely. the present invention provides a device and kit for positioning such objects. Of particular application in this case is the placement of indirectly fabricated restorations.

BACKGROUND OF THE INVENTION

There are many situations in life that require the accurate placement of small objects. Generally the accurate placement of a small object is hindered by a user's hands and an inability to control their grip and/or release on an object at a specific position. Examples of such situations include modelling and craft applications, i.e. scrap booking and jewellery making.

One situation that requires the accurate placement of a small object occurs in the dental field. Conventional techniques to secure inlays, onlays, crowns and veneers (dental restorations) have depended upon various rod-like handles tipped with sticky wax or nectar-like bulbs. These techniques are generally limited in their effectiveness due to their weak and unpredictable bond. Since the restoration once "held" by such handles is subject to multiple manipulations prior to final placement the tenuous bond provided by present alternatives is often stressed to the point of failure. The placement of these small dental restorations is the culmination of much effort and it is crucial that the grip described is reliable but also easily removable once final placement is achieved.

Different options have been discussed in the dental community to overcome some of the problems of the known methods discussed above. It is generally acknowledged that existing products are inadequate. One suggestion advanced has been to use a light cured bonding agent normally used to bond standard dental composite restorations. The technique suggested has been to bond a brush unto the restorative surface. This technique provides a more stable bond than other presently marketed techniques but is time consuming, requires two people to perform, and is not cost effective. The brush is also often difficult to remove after placement and residual bond left behind on the restoration is clear and hence difficult to see. Its complete removal after requires the use of a dental drill, which can mar the previously polished or glazed finish.

Another technique involves placement of a heat activated adhesive pellet unto the restoration. heat is then applied with a portable heating device until molten. A tool with a flocked or disc-ended tip is subsequently plunged into the liquefied adhesive to form a handle. This technique, although reliable and effective, requires the use of both hands. One to hold the restoration with the positioned adhesive pellet and the other to operate the heating device. A learning curve is experienced in developing the method as it is somewhat technique sensitive. Another potential problem is that battery power output will drop with repeated use of the device. This will slow the time required to liquify the adhesive and hence slow down the entire process. Another problem may arise when applying heat to adhesive pellets on smaller restorations. There is the slight risk of burning ones fingers as they will inevitably be in close proximity to the tip of the heating device. Thus there is a need for an improved method and for a device useful for object positioning.

SUMMARY OF THE INVENTION

In one embodiment, the present invention provides a placement tool that can be pre-loaded with a heat activated adhesive. In another embodiment, the present invention provides a pre-loaded placement tool comprising a heat activated adhesive.

In another embodiment, the present invention provides a placement tool for use with a heating device. The placement tool including at least one flange operable to cooperate with at least one bracket located on the heating device for placement of the placement tool on the heating device.

In another embodiment, the present invention provides a method for heating adhesive to be used in a restoration, comprising the steps of: (i) providing a placement tool having a body and a head portion, as described herein; (ii) placing the head portion of the placement tool into molten adhesive to form a pre-loaded placement tool; (iii) placing the pre-loaded placement tool on a heating device at a position operable to allow heat from the heating device to heat the pre-loaded adhesive; (iv) removing the pre-loaded placement tool from the heating device once the adhesive has been sufficiently heated.

In an alternative embodiment, the placement tool comprises a body having a head portion located at one end of the body, the head portion being operable to receive adhesive thereon. The placement tool further comprises at least one flange, extending around the body.

In another embodiment, the placement tool, described above, is operable to engage with a heating device. The heating device includes a heating element and at least one bracket. The at least one bracket is operable to engage with the placement tool described herein and specifically to engage with the at least one flange of the placement tool.

In a further embodiment, the heating device includes a bracket having at least two arms and the placement tool includes a pair of flanges. Each flange is configured to be received and held by the arms of the bracket.

In an alternative embodiment, the present invention provides a dental restoration kit comprising a placement tool comprising a body portion and a head portion located at one end of the body portion, and at least one flange surrounding the body portion, the head portion configured to receive adhesive thereon; and a heating device comprising a heating element and at least one moveable bracket configured to receive the placement tool thereon.

BRIEF DESCRIPTION OF THE DRAWINGS

The present invention will now be described in further detail with reference to the following figures:

FIG. 4 illustrates another side view of the configuration of FIG. 3 with the bracket in the lowered position.

DETAILED DESCRIPTION OF THE PREFERRED EMBODIMENTS

In one embodiment, the present invention provides a placement tool that is pre-loaded with adhesive that can be heat activated when required.

The placement tool includes a flexible body, also referred to as a handle, and a head portion which may be in the form of a flocked head, a bulb-like head, a flat head, a disc shaped head, a rectangular head or a squaretip head. It will be understood that the head portion is not limited to the shapes and forms described above. The placement tool may be preloaded with adhesive.

The loading process includes the steps of dipping the head portion into molten adhesive and allowing the drop of retained adhesive to set into a sphere like form that surrounds the retentive head portion. It will be understood that the adhesive drop will form around the head portion and take on the shape of the head portion. The adhesive may then be heat activated in a prep oven just before placement.

Figure 1:
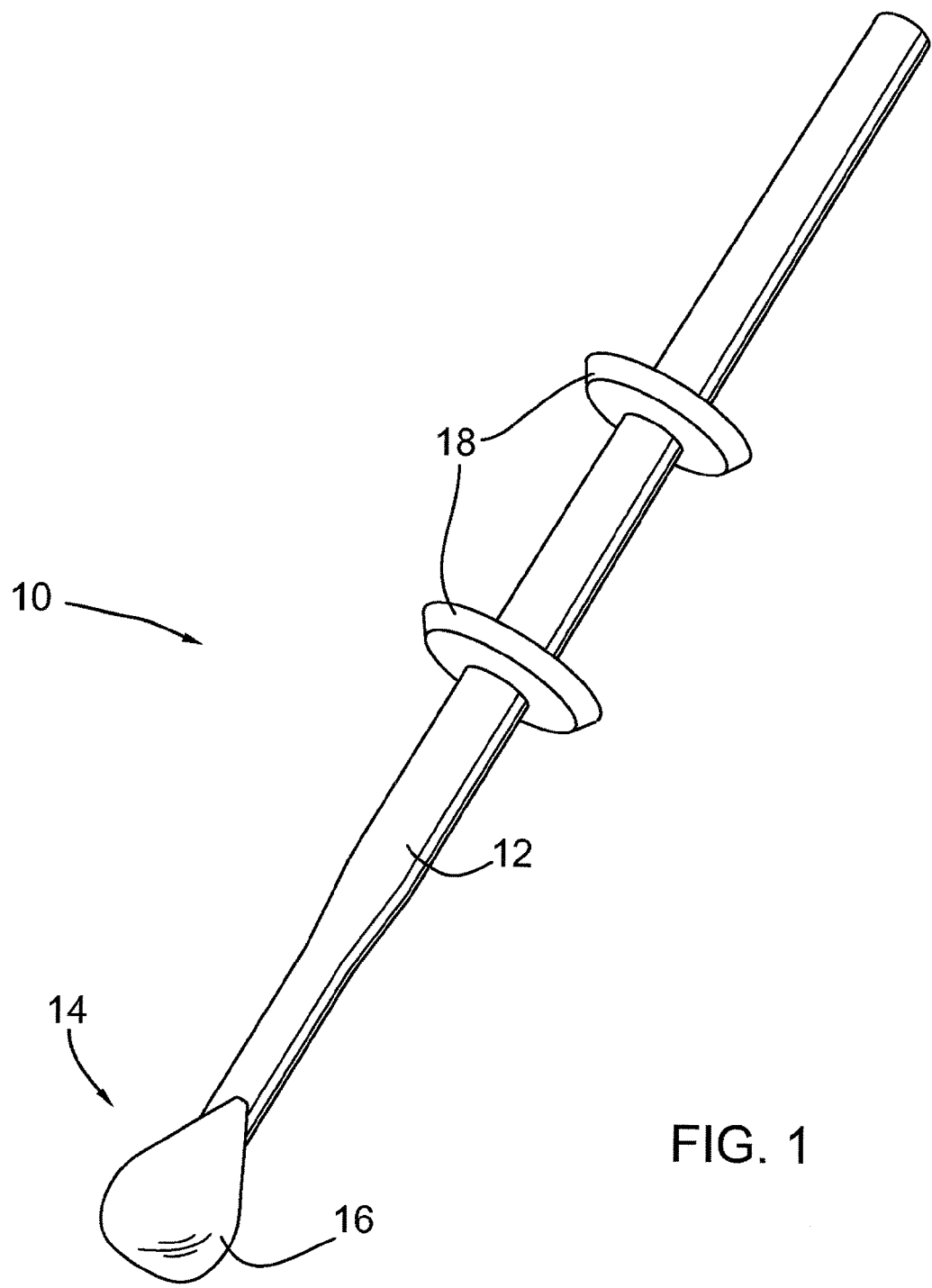
FIG. 1 illustrates one embodiment of a placement tool of the present invention.
Figure 2:
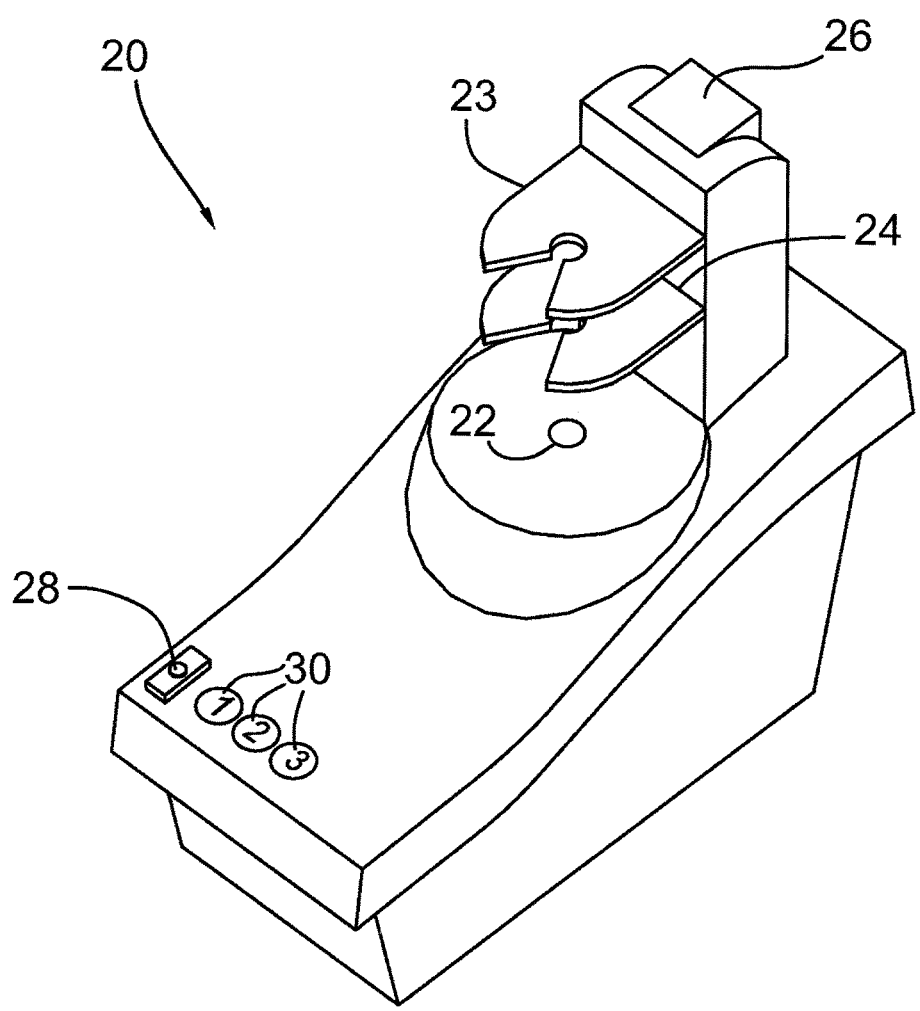
FIG. 2 illustrates one embodiment of the heating device to be used in combination with the placement tool of the present invention.

In one embodiment, the placement tool is used with a heating device, as shown in FIGS. 1 and 2. In this embodiment, the placement tool, indicated in FIG. 1 at numeral 10 includes a body 12 and a head portion 14. The head portion 14 may be shaped, as described above, and receives adhesive 16 thereon, as shown in FIG. 1. The placement tool 10 also includes at least one flange 18, for use in combination with the heating device, described further below. As seen in FIG. 1, the placement tool may include two flanges 18.

The heating device 20 is shown in FIG. 2 and includes a heating element, not specifically shown, contained within the chamber 20. The chamber 20 includes an opening 22 that allows for heat to be emitted from the heating element. The heating device 20 also includes a bracket 24 for receiving the placement tool 10. The bracket 24 may include one or more arms 23, shaped to receive the placement tool 10, and specifically to abut the at least one flange 18 located on the placement tool 10. The bracket 24 is spring loaded and operable to move up and down relative to the heating device 20. The bracket 24 includes a spring mechanism that allows for the bracket 24 to be held down adjacent, or within, the heating device 20. Release of the spring mechanism may be achieved by pressing a switch 26 that is connected to the spring mechanism and bracket 24. It will be understood that any type of releasable locking device may be used to hold the bracket in a lowered position and for releasing the bracket to a raised position, when required by the user.

The heating device 20 also includes an on/off switch, indicated generally at numeral 28, and one or more switches to control the time of heating, and/or the temperature of the heating element. Examples of these switches are indicated at numeral 30. It will be understood by a person skilled in the art that these switches are not limited to the look and location of those shown in the Figures and other variations, including size, shape and position, may be used and fall within the scope of this invention.

Figure 3:
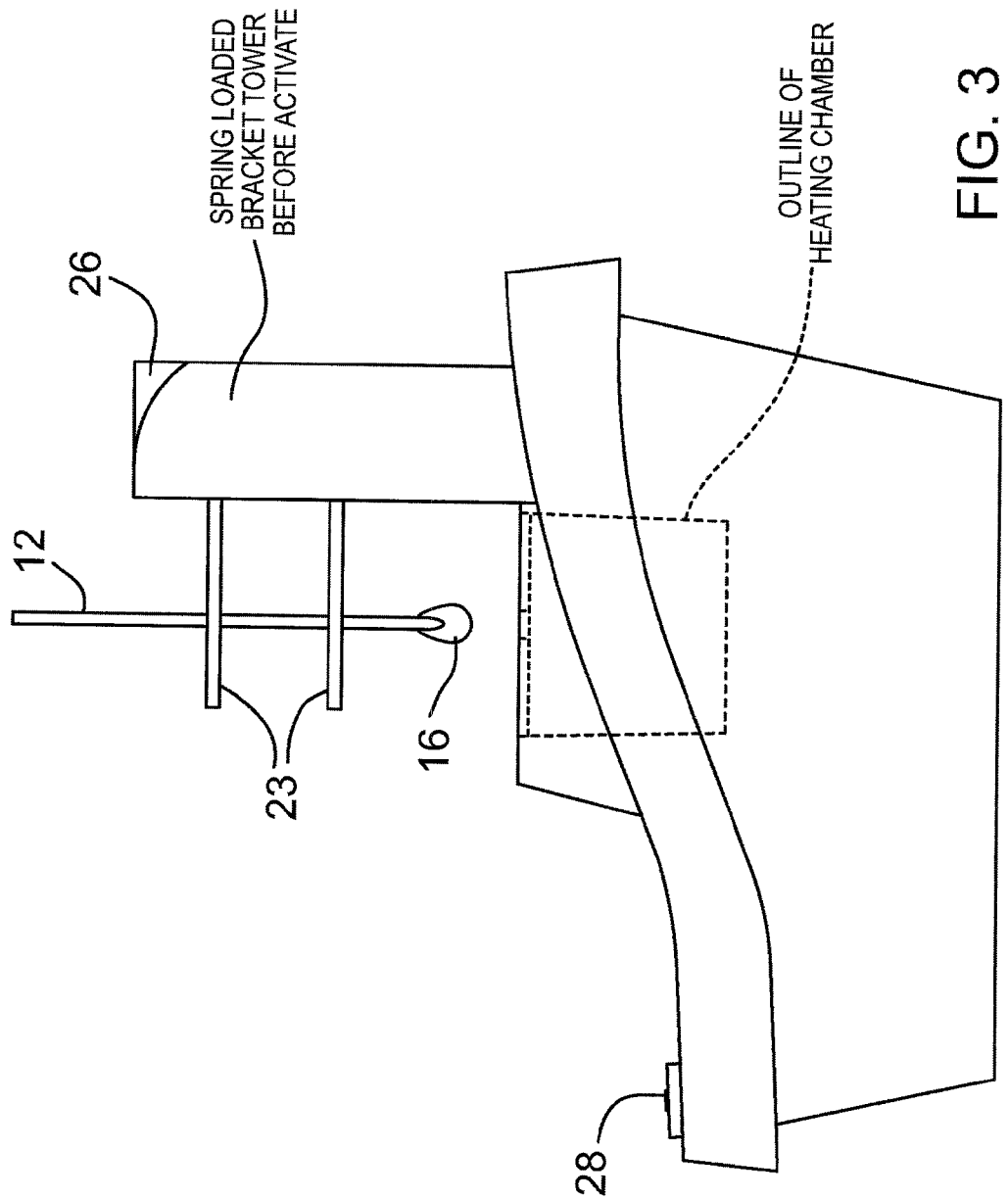
FIG. 3 illustrates a side view of the heating device of the present invention showing the placement tool received in the bracket on the heating device, the bracket being placed in the raised position.

As stated above, in one embodiment, the body 12 of the placement tool 10 includes at least one flange 18 to allow for placement of the placement tool 10 on the heating device 20. It will be understood that the placement tool 10 is placed in the holding bracket 24 with the head portion 14, including the adhesive, facing down, to be received in, or adjacent to, the opening 22 to receive heat from the heating element, shown in FIG. 3.

Once the placement tool 10 is placed in the holding bracket 24, with the at least one flange 18 resting against one of the arms of the bracket 24, the bracket 24 can then be lowered so that the adhesive tip can be placed adjacent to, or within, the opening 22 and likewise the heating element. This position is shown in FIG. 4 which illustrates the position of the preloaded adhesive on the head portion 14 within the opening 22 of the heating device 20.

It will be understood that the placement tool 10, and specifically the body 12, and the adhesive 16 may vary in colour according to size of tip. This enables a user to easily identify a tip size to match the size of the restoration to be retained.

In one embodiment, the heating device 20 emits an audible signal when heating of the adhesive is complete. The time chosen for the heating will correspond to the adhesive tip size. Larger tips requiring more heating time and vice versa. When ready the adhesive tipped placement tool 10 can be raised, away from the heating element, by pressing the switch 26, or release button, on the spring loaded bracket 24.

At this point the placement tool 10 with the heat softened tip can be removed from the bracket 24 and applied directly to the restoration to be secured. Hence a secure handle, or tool, is created quickly and with minimal manual technique required.

In one embodiment, to facilitate placement onto the heating device 24 the placement tool will include tapered flanges, as shown in FIG. 1. However, the flanges of the placement tool are not limited to having such flanges. The flexible body 12 of the placement tool 10 allows for the placement tool 10 to be bent to any desired angle to ease in placement after removal from the heating unit. The placement tool 10 and adhesive pellet will release together cleanly from the restoration when required by pulling on the body 12.

In one embodiment, heat will be generated in the heating device 20 by a series of heating coils or by intense light. The heating device 20 may have more than one chamber to accommodate the placement of multiple placement tools at one time. The heating device 20 may be powered by wall plug or be battery operated, or by any other means known in the art.

It will be understood from the above description that this device, besides facilitating the placement of dental restorations, may be useful in a myriad of other applications. Small items require attachment and transfer in many fields such as, but not limited to, arts and crafts, optometry, modelling and laboratory procedures.

While this invention has been described with reference to illustrative embodiments and examples, the description is not intended to be construed in a limiting sense. Thus, various modification of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

The invention claimed is:

1. A dental restoration kit comprising:
   a placement tool comprising a body portion and a head portion located at one end of the body portion, wherein the head portion is preloaded with adhesive which surrounds the head portion and which is in set form and wherein the head portion is not bound to the object to be positioned; and
   a heating device comprising a heating chamber that emits heat adapted to removably receive the head portion of the placement tool and at least one moveable bracket configured to receive the placement tool thereon, wherein the bracket is moveable to place the head portion of the placement tool into the heating chamber to melt the adhesive and moveable to remove the head portion of the placement tool from the heating chamber.

2. The dental restoration kit according to claim 1, wherein the placement tool includes at least one flange surrounding and protruding from the body portion.

3. The dental restoration kit according to claim 2, wherein the at least one moveable bracket includes at least one arm sized to receive the at least one flange of the placement tool thereon.

4. The dental restoration kit according to claim 1, wherein the heating device includes at least one opening to emit heat or receive the head portion of the placement tool.

* * * * *